United States Patent
von Corswant et al.

(10) Patent No.: US 7,491,836 B2
(45) Date of Patent: Feb. 17, 2009

(54) NON-IONIC SURFACTANTS FOR POORLY SOLUBLE MOLECULES

(75) Inventors: Christian von Corswant, Mölndal (SE); Karl Hult, Stockholm (SE); Erik Söderlind, Mölndal (SE); Fredrik Viklund, Stockholm (SE)

(73) Assignee: AstraZeneca AB, Sodertalje (SE)

( * ) Notice: Subject to any disclaimer, the term of this patent is extended or adjusted under 35 U.S.C. 154(b) by 155 days.

(21) Appl. No.: 10/553,275

(22) PCT Filed: Apr. 13, 2004

(86) PCT No.: PCT/SE2004/000572

§ 371 (c)(1),
(2), (4) Date: Oct. 13, 2005

(87) PCT Pub. No.: WO2004/089869

PCT Pub. Date: Oct. 21, 2004

(65) Prior Publication Data

US 2006/0287542 A1    Dec. 21, 2006

(30) Foreign Application Priority Data

Apr. 14, 2003  (SE) .................................. 0301119

(51) Int. Cl.
*C07C 59/00* (2006.01)
(52) U.S. Cl. .................. 554/213; 554/219; 554/227; 424/439; 514/784
(58) Field of Classification Search ............... None
See application file for complete search history.

(56) References Cited

U.S. PATENT DOCUMENTS 4,366,151 A    12/1982    Oppenlaender et al.
6,365,637 B1    4/2002    Zirnstein et al.

FOREIGN PATENT DOCUMENTS

EP    17059 B1    11/1981

OTHER PUBLICATIONS

Janssen et al., Biotech. Letters, "Lipase-Catalyzed Synthesis of oleic acid esters of polyethylene glycol 400", vol. 16, No. 2, pp. 163-168, 1994.*
Lorenz, W. et al., National Library of Medicine (NLM), file Medline, Medline accession No. 6177219.
STN International, file CAplus, CAplus accession No. 1999:431639, Document No. 131:86938.
Database WPI, Week 199624, Derwent Publications Ltd., London, GB, AN 1996-233354 & JP 80-89263 A.
Database WPI, Week 198422 Derwent Publications Ltd., GB; AN 1984-136506 & JP 59-069135A.
Database WPI, Week 199538 Derwent Publications Ltd., London GB; AN 1995-287977 & JP 71-84672A.
"The Theory and Practice of Industrial Pharmacy" $2^{nd}$ ed., Lea & Febiger, 1976, p. 108-111.
Lorentz et al., "Agents and Actions", vol. 12, ½, 1982, p. 64-80.
Vulfson, "Novel Surfactants", Holmberg editor, Marcel Dekker, 1988, p. 279-97.
Yalkowsky, "Solubility & Solubilization in Aqueous Media", American Chemical Society and Oxford University Press, 1999, p. 312-320.
"Surface Active Agents (non-ionic)- Determination of Polyethylene Glycols and Non-Ionic Active Matter (adducts)- Weibull Method", International Standard Organization, ISO-2268:1972(E).
US Pharmacopeia 24, 2000, p. 10.
Corswant et al., "Triglyceride Based Microemulsion . . . ", J. Pharm. Sci., 1998, 87(2), p. 200-8.
Mosharraf and Nyström, "The Effect of Particle . . . ", Int. J. Pharm., 1995, 122, p. 35-47.
Östh, Karin, Thesis: The Horizontal Ussing Chamber Method in Studies of Nasal Drug Delivery, 2002, Faculty of Pharmacy, Uppsala University; and attached papers: Paper I: Östh et al., J. Pharm. Sci., vol. 91, No. 5, May 2002 Paper II: Östh et al., J. Controlled Release, 83, (2002), 377-388 Paper III: Östh et al., "Uptake of ovalbumin-conjugated starch microparticles by pig respiratory nasal mucosa in vitro" (manuscript submitted for publication) Paper IV: Östh et al., "Correlation between epithelial toxicity and surfactant structure derived from studies of polyoxyethylene oxide and their effects on Caco-2 cells and pig nasal mucosa" (manuscript).

* cited by examiner

*Primary Examiner*—Deborah D Carr
(74) *Attorney, Agent, or Firm*—White & Case LLP

(57) ABSTRACT

New non-ionic surfactants in the form of polyoxyalkylene glycol hydroxy fatty acid derivatives or monoalkylated polyoxyalkylene glycol hydroxy fatty acid derivatives having a polyoxyalkylene/alkyl polyoxyalkylene chain with a chain-length of 25-455 repeating units and a specified substituent on the hydroxy position of the specified hydroxy fatty acid, according to the general formula (I) $CH_3$—$(CH_2)_x$—$CH$—$(CH_2)_y$—$CO$—$[$—$O$—$R_3$—$]_z$—$O$—$R_1$ $R_2$—$O$ (I); wherein for example $R_1$ is methyl, $R_2$ is optionally substituted $C_{14}$-$C_{22}$ acyl, alkyl, or alkenyl, $R_3$ is ethylene, x is 2-12, y is 7-17, (x+y) is 3-19 and z is 25-57; advantageously prepared by involving an enzymatic process, formulations comprising them, their use as solubilizers and a process involving a hydrolytic enzyme for preparing them.

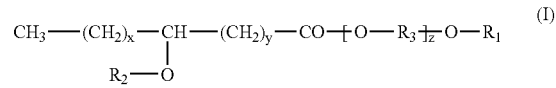

(I)

14 Claims, No Drawings

US 7,491,836 B2

NON-IONIC SURFACTANTS FOR POORLY SOLUBLE MOLECULES

TECHNICAL FIELD

This invention relates to polyoxyalkylene glycols (in the following sometimes referred to as POAG) or monoalkylated polyoxyalkylene glycols esterified with O-acylated, O-alkylated or O-alkenylated hydroxy fatty acids, as well as their manufacture, their use in formulations (including pharmaceutical formulations), and their use as surfactants.

BACKGROUND OF THE INVENTION

The introduction of HTS methods (High Throughput Screening) in early drug discovery together with an enhanced demand on selectivity have in recent years increased the number of candidate drugs with a low aqueous solubility. In order to minimise administration volumes and obtain a high bioavailability it is of great practical importance for pharmaceutical formulators to have the ability to increase the solubility of these compounds when suitable dosage forms are developed. These preparations can be intended both for assessment of medical effect in humans and safety studies in animals during the development of a new drug, and as the final pharmaceutical dosage form for the marketed product.

One commonly used method to increase the solubility of poorly soluble compounds is to solubilize the compound in a micellar system by the use of surfactants. ["The Theory and Practice of Industrial Pharmacy" $2^{nd}$ ed. Lea & Febiger, 1976, p. 108-111.]

The main advantages with micellar systems are the stability over a wide composition range, simplicity of preparation, low viscosity and the fact that a micellar system is a thermodynamically stable single phase which is optically clear. Surfactants can be divided into anionic, e.g. sodium lauryl sulfate, cationic, e.g. cetyl trimethyl-ammonium bromide, zwitter-ionic, e.g. alkyl betaines and non-ionic surfactants, e.g. ethoxylated sorbitanoleate, according to their chemical properties.

The choice of surfactants for use in pharmaceutical applications depends to some extent on the route of adminstration and is rather limited since most surface-active compounds are not tolerated well enough for pharmaceutical use. For parenteral use ionic surfactants are not suitable since these cause hemolysis of red blood cells and destruction of T lymphocyte cells at low concentrations. ["Solubility & Solubilization in aqueous media.", Yalkowsky, 1999]. The most accepted surfactants for parenteral use are phospholipids and non-ionic surfactants. For oral use non-ionic surfactants are usually preferred but ionic-surfactants have been used in low concentrations.

Non-ionic surfactants used in pharmaceutical applications today include substances/mixtures such as ethoxylated castor oil (Cremophor EL), ethoxylated sorbitan fatty acid esters, e.g. polyoxyethylene sorbitan monooleate (Tween 80), sorbitan fatty acid esters, e.g. sorbitan monooleate (Span 80), ethoxylated hydroxystearic acid, e.g. polyethylene glycol 660 (12-)hydroxystearate (Solutol HS15), etylene and propylene oxide block copolymers (Pluronic F68) and fatty acid esters of glycerol (Imwitor 742).

The above described non-ionic surfactants which are presently used in pharmaceutical applications do, however, exhibit a number of disadvantages.

For example, the commercial non-ionic surfactants available for pharmaceutical formulators are complex mixtures of different molecules which makes the characterisation of these products very difficult, giving an expensive and tedious analytical process to ensure adequate quality (for i.a. pharmaceutical applications).

Recent studies on adverse effects on epithelial cells have shown that commercial non-ionic surfactants have a profound effect on epithelial cells in concentrations typically used for solubilisation (Östh, Karin, Thesis: The horizontal Ussing chamber method in studies of nasal drug delivery, 2002. Faculty of Pharmacy, Uppsala University).

It is also well known that surface-active compounds often cause hemolysis at low concentrations when administered parenterally.

The existing non-ionic surfactants systems used for parenteral administration are all based on polyethylene glycol derivatives. Although there are several pharmaceutical products for parenteral administration on the market containing these surfactants, they all suffer from quite severe side effects, like release of histamine which in severe cases can lead to anaphylactic chocks (Lorentz et al., Agents and Actions, Vol. 12, 1/2, 1982).

Histamine release is believed to be caused by impurities in the commercial products and since the non-ionic surfactants used are very complex mixtures of different molecules it is not possible to purify existing products. Also in such situations it is hard to relate any side-effects to a particular molecule. (Vulfsson. In "Novel Surfactants". Holmberg editor. Marcel Dekker 1988. p. 279-97.)

In EP 0017059 A1, reaction products of monohydroxy fatty acids with ethylene oxide in a given molar ratio are mentioned (the Solutol® type of compounds).

The products formed are mixtures of monoesters or diesters of polyetylene glycol (PEG) and monohydroxy fatty acids or estolides, the latter commonly known as a generic name for linear oligomeric polyesters of hydroxyl fatty acids wherein the carboxyl group and hydroxyl group of hydroxyl fatty acids are dehydrated to form oligomers. The products of EP 0017059A1 comprising two or more monohydroxy fatty acids where the monohydroxy fatty acid of the estolide may either be attached directly to the hydroxyl group of another fatty acid or to a hydroxyl group of a PEG chain attached to the aforementioned hydroxyl group of a monohydroxy fatty acid. These reaction products are stated to be used especially as dissolution enhancers for pharmaceutical purpose. With these kind of compounds, the resulting synthesis product will always be a mixture of compounds. Solutol HS 15 is such a product. Short PEG chains (one type of polyoxyalkylene glycol, or POAG, chain) are a characteristic feature of the compounds claimed in EP 0017059 A1.

U.S. Pat. No. 6,365,637 claims the use of esters or amides of hydroxylated carboxylic acids as solubilizers, for i.a. pharmaceutical purposes. These compounds all have short PEG chains. Furthermore, the optional use of a dimerized fatty acid, as described in U.S. Pat. No. 6,365,637, of commercial quality including both monomeric, dimeric, trimeric and higher polymerized acids in the synthesis is a draw-back when one desires to obtain highly pure compounds.

DESCRIPTION OF THE INVENTION

Accordingly, there is a need for new effective non-ionic surface-active compounds not having the above mentioned disadvantages of being complex mixtures, or potential for inducing adverse reactions seen as e.g. epithelial cell interaction, histamine release or hemolysis.

As some side-effects are believed to be caused by impurities in the commercial products and as the non-ionic surfactants used are very complex mixtures of different molecules it is not possible to purify existing products (Vulfsson. In "Novel Surfactants". Holmberg editor. Marcel Dekker 1988. p. 279-97.). Therefore, there is need for new "non-toxic" and well-defined surfactants having high solubilization capacity, for use as solubilizers of poorly soluble drug molecules. Such compounds may have use in both pharmaceutical and other fields.

It is also a need for a method of synthesis that permits the surfactant to be manufactured as a highly pure compound.

Furthermore, there is also a need for these compounds with an improved profile regarding side-effects and having high solubilization capacity as surfactants, for use in formulations generally, but especially for use in pharmaceutical formulations.

It has now surprisingly been found that compounds being an O-acylated or O-alkylated/O-alkenylated hydroxy-fatty acid (hydroxy-fatty acid in the following also referred to as "HFA"), esterified with polyoxyalkylene glycol (POAG) or monoalkylated POAG, where the POAG (or its derivative) has a specified average chain-length are better tolerated than compounds of the prior art, especially with regard to low haemolytic activity and lack of interaction with epithelial cells (CACO-2 cells). Furthermore they can be prepared as well-defined compounds and they are very effective as solubilisers. Such compounds can advantageously be used in i.a. pharmaceutical formulations such as tablets, capsules, powders, dispersions, emulsions, rectal formulations like suppositories and also in solutions. In addition they can be used as e.g. media for making solid dispersions, absorption enhancers, emulsifiers in emulsions and microemulsions, dispersing agents in solid dispersions, emulsifier in self-emulsifying systems, lubricants in tablet pressing, wetting agents in granulation processes, vehicles in spray-drying compositions etc, are also uses, not limited to any particular administration route, that are contemplated in this invention.

It has also been found that a process involving an enzymatic step connecting a previously formed O-acyl HFA or O-alky/O-alkenyl HFA (or esters of such a HFA or their derivatives) with POAG or alkylPOAG (e.g. MePEG1200, also known as polyethylene glycol monomethyl ether with average molecular weight 1200) using a hydrolytic enzyme, said enzyme having the capability of catalyzing ester formation between the carboxylic group of the HFA-derivative and the ending hydroxyl group of POAG or POAG-derivative, without catalyzing any reaction with existing ester or ether bond on the O-acyl/alkyl/alkenyl-HFA (or corresponding derivative). As an example, lipase B from *Candida antarctica* or an equivalent can be used. This enzyme is particularly beneficial to employ to obtain more homogenous reaction products. Another advantage is that it makes it possible to employ a reaction for this esterification step that is free from organic solvents.

DETAILED DESCRIPTION OF THE INVENTION

The compounds of the invention, surprisingly having the beneficial advantages of better tolerability, low hemolytic activity, possibility to be produced with higher purity and having high solubilization capacity, have chemical structures as described in formula (I) below;

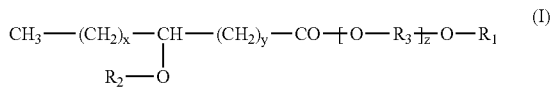

The compounds are based on an acylated/alkylated/alkenylated hydroxy fatty acid forming an ester bond with a poly (oxyalkylene) glycol [in a shorter form POAG] or monoalkylated poly (oxyalkylene) glycol on the carboxylic group end.

The $R_1$ group positioned on the outer end of the POAG chain may be H or $C_1$-$C_4$ alkyl. In one aspect of the invention $R_1$ is H, alternatively $R_1$ is $C_1$-$C_4$ alkyl. In one preferred embodiment of the invention, the $R_1$ is H or $C_1$-$C_2$ alkyl. In a more preferred embodiment of the invention $R_1$ is $C_1$-$C_2$ alkyl. In a most preferred embodiment the $R_1$ is methyl.

The term POAG includes poly (oxyethylene) glycols, commonly known as i.a. PEG's, and poly (oxypropylene) glycols, commonly known as PPG's. The oxypropylene units may be linear or branched.

Thus, $R_3$ is chosen among ethylene, propylene or branched propylene.

The POAG chain used in the invention has preferably, counted as poly (ethylene) glycol, an average molecular weight of 1100-20000. More preferred is to use a POAG with an average molecular weight of 1100-10000, most preferred is to use a POAG with an average molecular weight of 1100-2500, all these average molecular weights counted as for poly (ethylene) glycol.

These average molecular weights are counted as excluding the weight of any alkyl groups in the alkyl-derivatized POAG's.

The poly (oxyalkylene) glycols or monoalkylated poly (oxyalkylene) glycols used are of pure, monodisperse or polydisperse commercial quality.

The above range limits given for polyoxyalkylene glycol (e.g. PEG) chain average molecular weight, corresponds to values of z being 25-455, preferably 25-228 and most preferably 25-57.

Table 1 below shows the relation between z and average molecular weight for PEG and PPG, respectively.

TABLE 1

| z | Molecular weight Polyoxyethylene Glycol (PEG) | Molecular weight Polyoxypropylene Glycol (PPG) | Remark |
|---|---|---|---|
| 1 | 44 | 58 | As monomer unit |
| 25 | 1100 | 1450 | As multiples of monomer units |
| 57 | 2508 | 3306 | As multiples of monomer units |
| 100 | 4400 | 5800 | As multiples of monomer units |
| 228 | 10032 | 13224 | As multiples of monomer units |
| 455 | 20020 | 26390 | As multiples of monomer units |
| 500 | 22000 | 29000 | As multiples of monomer units |

The carbon chain in the hydroxy fatty acid part of the inventive compounds are characterized in that the oxygen from the hydroxy group is positioned such as that x is 2-18 and y is 1 to 17, while the sum of (x+y), defining the length of the hydroxy fatty acid carbon chain, is 3-19.

More preferably the value of x is 2-15 and the value of y is 4-17, while the sum of (x+y) is 6-19.

Most preferably the value of x is 2-12 and the value of y is 7-17, while the sum of (x+y) is 9-19.

The oxygen in the hydroxyl group on the HFA residue is connected (via an ester linkage or ether linkage) to a group $R_2$, $R_2$ being $C_{14}$ to $C_{22}$, linear or branched, acyl, alkyl or alkenyl wherein the acyl, alkyl or alkenyl may be optionally further substituted with one or more of the following (independently selected); halogen, cyano, carboxy, carbamoyl, carbamoyl ($C_1$-$C_4$)alkyl, fluoromethyl, difluoromethyl, trifluoromethyl, mercapto, nitro, amino, ($C_1$-$C_4$)alkylamino, phenyl, naphthyl, phenyloxy, naphthyloxy, ($C_1$-$C_4$)alkylthio, or ($C_1$-$C_4$) alkylsulfinyl.

In one embodiment $R_2$ is unsubstituted. In another embodiment $R_2$ is substituted by one or two substituents, preferably one.

In another second embodiment of the invention, the $R_1$ group positioned on the outer end of the POAG chain is $C_1$-$C_4$ alkyl. In one more preferred second embodiment of the invention, $R_1$ is $C_1$-$C_2$ alkyl. In the especially most preferred second embodiment $R_1$ is methyl.

The term POAG includes poly (oxyethylene) glycols and poly (oxypropylene) glycols. The oxypropylene units may be linear or branched.

Thus, $R_3$ is chosen among ethylene, propylene or branched propylene.

The POAG chain used in the invention has preferably, counted as poly (ethylene) glycol, an average molecular weight of 1100-20000. More preferred is to use a POAG with an average molecular weight of 1100-10000, most preferred is to use a POAG with an average molecular weight of 1100-2500, all these average molecular weights counted as for poly (ethylene) glycol.

These average molecular weights are counted as excluding the weight of any alkyl groups in the alkyl-derivatized POAG's.

The poly (oxyalkylene) glycols or monoalkylated poly (oxyalkylene) glycols used are of pure, monodisperse or polydisperse commercial quality.

The above range limits given for polyoxyalkylene glycol (e.g. PEG) chain average molecular weight, corresponds to values of z being preferably 25-455, more preferably 25-228 and most preferably 25-57.

Table 1 above shows the relation between z and average molecular weight for PEG and PPG, respectively.

The carbon chain in the hydroxy fatty acid part of the inventive compounds are characterized in that the oxygen from the hydroxy group is positioned such as that x is 2-18 and y is 1 to 17, while the sum of (x+y), defining the length of the hydroxy fatty acid carbon chain, is 3-19.

More preferably the value of x is 2-15 and the value of y is 4-17, while the sum of (x+y) is 6-19.

Most preferably the value of x is 2-12 and the value of y is 7-17, while the sum of (x+y) is 9-19.

The oxygen in the hydroxyl group on the HFA residue is connected (via an ester linkage or ether linkage) to a group $R_2$, $R_2$ being $C_{14}$ to $C_{22}$, linear or branched, acyl, alkyl or alkenyl wherein the acyl, alkyl or alkenyl may be optionally further substituted with one or more of the following; halogen, cyano, carboxy, carbamoyl, carbamoyl($C_1$-$C_4$)alkyl, fluoromethyl, difluoromethyl, trifluoromethyl, mercapto, nitro, amino, ($C_1$-$C_4$)alkylamino, phenyl, naphthyl, phenyloxy, naphthyloxy, ($C_1$-$C_4$)alkylthio, or ($C_1$-$C_4$)alkylsulfinyl.

In one second embodiment $R_2$ is unsubstituted. In another second embodiment $R_2$ is substituted by one or two substituents, preferably one.

Synthesis

Ester Derivatization of Hydroxy Fatty Acid

The synthesis can, for example, be performed by starting from the hydroxy fatty acid or its $C_1$-$C_4$ alkyl esters. If needed, the hydroxy fatty acid starting material may be purified by a suitable method, e.g. extraction or chromatographic methods. This is beneficial for obtaining the best results of the invention.

Esterification of the fatty acid hydroxyl group can for example be performed with an acyl chloride. The two reactants are mixed in a suitable solvent, e.g. methyl tert-butyl ether (MTBE) containing pyridine in a suitable concentration e.g. 1.5 equivalents, in relation to the acyl chloride.

Purification of this product can for example be done by extraction. Suitably, the product is first washed with a weakly acidic solution, e.g. 1% sulphuric acid, and then with a weakly basic solution, e.g. saturated aqueous sodium bicarbonate. If needed, further purification may be done using a chromatographic method, e.g. preparative silica gel chromatography.

Other methods known in the state of the art can equally well be used to accomplish esterification of the fatty acid hydroxyl group.

Ether Derivatization of Hydroxy Fatty Acid

The synthesis can, for example, be performed by starting from esters of the hydroxy fatty acid. If needed, the hydroxy fatty acid ester may be purified by a suitable method, e.g. extraction or chromatographic methods. This is beneficial for obtaining the best results of the invention.

Etherification of the fatty acid hydroxyl group with an alcohol can for example be performed in two steps. The first step may consist of reacting the alcohol with toluene-4-sulfonyl chloride in a suitable solvent, e.g. dichloromethane, containing pyridine in a suitable concentration e.g. 1.5 equivalents in relation to the toluene-4-sulfonyl chloride. Purification of the produced alcohol toluene-4-sulfonate can for example be done by extraction. Suitably, the product is then washed with a weakly acidic solution, e.g. 1% sulphuric acid. If needed, further purification may be done using a chromatographic method, e.g. preparative silica gel chromatography.

The second step may consist of reacting the alcohol toluene-4-sulfonate with the hydroxyl fatty acid ester in a suitable system of solvent, base and catalyst, e.g. in acetonitrile containing 1 equivalent potassium carbonate and 0.05 equivalents sodium iodide, in relation to the alcohol toluene-4-sulfonate. Purification of the produced alkyloxy acid ester can for example be done by extraction. Suitably, the product is then washed with a weakly acidic solution, e.g. 1% sulphuric acid. If needed, farther purification may be done using a chromatographic method, e.g. preparative silica gel chromatography.

Other methods known in the state of the art can equally well be used to accomplish etherification of the fatty acid hydroxyl group.

Esterification with POAG or POAG Derivatives

One very advantageous succeeding step after the esterification or etherification of the HFA, yielding surprisingly pure products at high yield is when the obtained HFA derivatives are esterified with the polyoxyalkylene glycol, or monoalkylated polyoxyalkylene glycol using a hydrolytic enzyme, and this enzyme is having the capability of catalyzing ester formation between the carboxylic group of the HFA derivative and the ending hydroxyl group of POAG or POAG-derivative, without catalyzing any reaction with existing ester or ether bond on the O-acyl/allyl/alkenyl-HFA. This is in the following some times referred shortly to as "enzymatic POAGylation". As an example, lipase B from *Candida antarctica* or an equivalent can be used. A preferred enzyme to be used in the inventive process is lipase B from *Candida antarctica*. The most preferred form of the enzyme to be used in the inventive process is the immobilized form of the lipase B enzyme from *Candida antarctica*.

The enzymatic POAGylation step is advantageously performed in combination with the use of vacuum to remove water or any other volatile co-product formed during the esterification. This enzymatic POAGylation step can advantageously be performed without the presence of any organic solvents, i.e. a solvent-free reaction step.

The reaction can be monitored by using HPLC. A preferred option is to choose reversed phase chromatography, using an evaporative light scattering detector.

Reaction temperatures when utilizing lipase B from *Candida antarctica*, are typically between 50 and 90 degrees Celsius.

Formulations

The compounds of the invention may be incorporated for different purposes in formulations, thereby taking advantage of their benefits as described above. Such purposes include usages as; surface active agents, solubilizers, detergents, dispersants for liquid dispersions, solid dispersants, emulsifiers, carriers, freeze-drying additives, spray-drying additives and wetting agents.

The compounds of the invention can be used in combination with any other compound not being negatively influenced by their presence. Especially it is foreseen to use them in combination with compounds in water being (according to definition given in US Pharmacopoeia 24, from 2000, page 10) sparingly soluble or less soluble. This includes sparingly soluble, slightly soluble, very slightly soluble, practically insoluble and insoluble, according to the same definition. Thus it includes compounds having a solubility of less than approx. 0.033 mg/mg in a solvent, corresponding to 33 mg/ml in water. The solvent in relation to this invention is water, at 25 degrees Celsius and normal atmospheric pressure.

Pharmaceutical Formulations

The compounds of the invention may be incorporated in pharmaceutical formulations for any purpose known according to the art, thereby taking advantage of their benefits as described above. Such purposes include, but are not limited to using them as; surface active agents, solubilizers, emulsifiers, carriers, solid dispersants, dispersants for liquid dispersions, wetting agents, lubricants, freeze-drying additives, spray-drying additives, etc.

As such they may be included in parenteral formulations (e.g. subcutaneous, intravenous, intramuscular, intraperitoneal, intraarterial, intracerebrovascular), oral formulations, rectal formulations, topical formulations, buccal formulations, sublingual formulations, this enumeration not intended to be limiting in any way.

Preferred formulations are oral, topical, rectal or parenteral. More preferred formulations are oral or parenteral. Most preferred is parenteral formulations.

Non-limiting examples of oral formulations suitable for use with compounds of the invention are tablets, effervescent tablets, capsules, granules, pellets, powders, sachets, dispersions, suspensions, emulsions, microemulsions, self-emulsifying systems and solutions.

In the use of the compounds according to the invention, the formulator may need to include various excipients, such as cosolvents, buffers, polymers, disintegrants, fillers/diluents, stabilisers and preservatives.

The compounds of the invention can be used in combination with any pharmaceutically active ingredient (drug) or vitamin not being negatively influenced by their presence. Especially is it foreseen to use them in combination with drugs or vitamins in water being (according to definition given in US Pharmacopoeia 24, from 2000, page 10) sparingly soluble or less soluble. This includes sparingly soluble, slightly soluble, very slightly soluble, practically insoluble and insoluble, according to the same definition. Thus it includes drugs or vitamins having a solubility of less than approx. 33 mg/mg in a solvent, corresponding to 33 mg/ml in water. The solvent in relation to this invention is water, at 25 degrees Celsius and normal atmospheric pressure.

According to a further embodiment the pharmaceutical formulations may comprise one or more compound according to the invention, and may also contain more than one pharmaceutically active ingredient. It is further possible for the pharmaceutical formulations (utilizing the invention) to comprise one or more vitamin. Another aspect that is contemplated is that combinations of one or more vitamin with one or more pharmaceutically active ingredient may be used in the formulations of the invention.

A preferred embodiment of pharmaceutical formulation according to the invention comprises one or more drug or pharmaceutically active ingredient selected among; Proton pump inhibitors, calcium channel blockers, adrenergic beta-blockers, anesthetics, steroids, antioxidants, renin inhibitors, alkaloids, cytostatics, anticoagulants, lipid regulating agents, anti-depressants, neuroleptics, immunosuppressants, immunomodulators, antibiotics and non-steroidal antiinflammatory agents.

The following examples are provided to illustrate the present invention.

EXAMPLE 1

Synthesis of PEG600 mono-12-lauroyloxy-stearate

In general the reaction followed the way;
12-hydroxystearic acid→ethyl 12-hydroxystearate→ethyl 12-lauroyloxy-stearate→PEG600 mono-12-lauryloxy-stearate.

Ethyl 12-hydroxystearate.

Technical grade 12-hydroxystearic acid (purchased from Aldrich) was purified to >99% by extraction with hexane.

150 mmol (45 g) of the purified 12-hydroxystearic acid and 5 mmol (0.5 g) sulfuric acid was dissolved in 300 ml ethanol in a 500 ml round flask with a Dimroth condenser and refluxed at 78° C. for 20 hours. The product was isolated by solvent evaporation and subsequent dissolution in 300 ml methyl tert-butyl ether (hereinafter MTBE). The liquid was extracted with water (3×100 ml) and then evaporated. The product was recovered in 96% isolated yield (47.8 g).

Ethyl 12-lauroyloxy-stearate.

20 mmol (6.57 g) of the obtained ethyl 12-hydroxystearate and 30 mmol (2.4 g) pyridine was dissolved in 200 ml MTBE at 50° C. in a 250 ml round flask with a Dimroth condenser and drying tube. Under stirring, 19.4 mmol (4.24 g) lauroyl chloride (from Sigma Aldrich) was added slowly and allowed to react for 5 hours. The reaction was stopped by lowering the temperature to 25° C. and adding 100 ml water.

The solution was extracted three times with 50 ml portions of 1% aqueous sulfuric acid, followed by extraction with saturated aqueous sodium bicarbonate (90 g/l, 3×50 ml) and finally water (3×50 ml). Remaining solvent was removed by evaporation.

Released lauric acid was removed by chromatography on silica gel eluting with 5% ethyl acetate in cyclohexane with 0.1% acetic acid. Afterwards the solvent was evaporated.

Ethyl 12-lauroyloxy-stearate was recovered in 71% (7.1 g) isolated yield.

PEG600 mono-12-lauroyloxy-stearate.

7.5 mmol (3.7 g) of the obtained ethyl 12-lauroyloxy-stearate and 75 mmol (45 g) PEG600 were mixed with 50 mg immobilized lipase B from *C. antarctica* (Novozym 435 from Novozymes A/S Denmark) in a 250 ml round flask with stirring under vacuum (<1 mm Hg) at 60° C. for 16 h.

The reaction was monitored using reversed phase HPLC with a Supelco Discovery C18-column (4.6 mm i.d.×150 mm), 1 ml/min of a 95:5 methanol:water mixture with addition of 0.5% acetic acid in the separation. Detection was done with a Sedex 45 evaporative light scattering detector (Sedere, Alfortville, France) at 30° C. and 2 bar air pressure.

Afterwards the enzyme was removed by filtration and the product was extracted with ethyl acetate and saturated aqueous sodium chloride according to ISO-2268 ["Surface active agents (non-ionic)—Determination of polyethylene glycols and non-ionic active matter (adducts)—Weibull method", International Standard Organization, ISO 2268:1972] but at room temperature followed by solvent evaporation, dissolution in dry ethyl acetate, filtration and evaporation. PEG600 mono-12-lauroyloxy-stearate was recovered in 93% (7.2 g) isolated yield.

EXAMPLE 2

Synthesis of PEG600 mono-12-propionyloxy-stearate

In general the reaction followed the way;
12-hydroxystearic acid→12-propionyloxy-stearic acid→4 PEG600 mono-12-propionyloxy-stearate.

12-Propionyloxy-stearic Acid.

Technical grade 12-hydroxystearic acid (purchased from Aldrich) was purified to >99% by extraction with hexane.

10 mmol (3.0 g) of the purified 12-hydroxystearic acid and 25 mmol (2.0 g) pyridine were dissolved in 150 ml MTBE at 50° C. in a 250 ml round flask with a Dimroth condenser and drying tube. Under stirring, 13 mmol propionyl chloride (from Sigma Aldrich) was added slowly and allowed to react for 19 hours. The reaction was stopped by lowering the temperature to 25° C. and adding 50 ml water.

The solution was extracted with 1% aqueous sulfuric acid (3×25 ml) followed by saturated aqueous sodium bicarbonate (90 g/l, 3×25 ml) and water (3×25 ml). Remaining solvent was removed by evaporation. 12-Propionyloxy-stearic acid was recovered in 97% (3.47 g) isolated yield.

PEG600 mono-12-propionyloxy-stearate.

9.9 mmol (3.7 g) 12-propionyloxy-stearic acid and 99 mmol (59.5 g) PEG600 were mixed with 50 mg immobilized lipase B from *C. antarctica* (Novozym 435 from Novozymes A/S Denmark) in a 250 ml round flask with stirring under vacuum (<1 mm Hg) at 60° C. for 21 hours.

The enzyme was removed by filtration and the product was extracted with ethyl acetate and saturated aqueous sodium chloride according to ISO-2268 [1972] but at room temperature followed by solvent evaporation, dissolution in dry ethyl acetate, filtration and evaporation. PEG600 mono-12-propionyloxy-stearate was recovered in 78% (7.5 g) isolated yield.

EXAMPLE 3

Synthesis of PEG1500 mono-12-stearoyloxy-stearate

In general the reaction followed the way;
12-hydroxystearic acid→ethyl 12-hydroxystearate→ethyl 12-stearoyloxy-stearate→PEG1500 mono-12-stearoyloxy-stearate.

The 12-hydroxystearic acid was from the same origin and purified as in the preceding examples.

Ethel 12-hydroxystearate
Was obtained according to Example 1.

Ethyl 12-stearoyloxy-stearate 10 mmol (3.29 g) ethyl 12-hydroxystearate and 15 mmol (1.2 g) pyridine were dissolved in 100 ml MTBE at 50° C. in a 250 ml round flask with Dimroth condensers and drying tubes.

Under stirring, 9.7 mmol stearoyl chloride (2.94 g) was added slowly. The reaction was stopped after 15 hours by lowering the temperature to 25° C. and adding 50 ml water.

The solution was extracted with 1% aqueous sulfuric acid (3×25 ml) and remaining solvent was removed by evaporation.

Released stearic acid was removed by chromatography on silica gel eluting with a gradient from 5% to 10% ethyl acetate in cyclohexane fortified with 0.1% acetic acid followed by evaporation of the solvent.

Ethyl 12-stearoyloxy-stearate was recovered in 81% (4.7 g) isolated yield.

PEG1500 mono-12-stearoyloxy-stearate 7.8 mmol (4.7 g) ethyl 12-stearoyloxy-stearate was mixed with 100 mmol (150 g) PEG1500 and 50 mg immobilized *C. antarctica* lipase B in a 500 ml round flask with stirring under vacuum (<1 mm Hg) at 75° C. for 39 hours.

The enzyme was removed by filtration and the product was extracted with ethyl acetate and saturated aqueous sodium chloride according to ISO-2268 [1972] at room temperature followed by solvent evaporation, dissolution in dry ethyl acetate, filtration and evaporation. PEG1500 mono-12-stearoyloxy-stearate was recovered in 71% (11.4 g) isolated yield.

EXAMPLE 4

Synthesis of PEG1500 mono-12-oleoyloxy-stearate

In general the reaction followed the way;
12-hydroxystearic acid→ethyl 12-hydroxystearate→ethyl 12-oleoyloxy-stearate→PEG1500 mono-12-oleoyloxy-stearate.

The 12-hydroxystearic acid was from the same origin and purified as in the preceding examples.

Ethyl 12-hydroxystearate
Was obtained according to Example 1.

Ethyl 12-oleoyloxy-stearate 10 mmol (3.29 g) ethyl 12-hydroxystearate and 15 mmol (1.2 g) pyridine were dissolved in 100 ml MTBE at 50° C. in a 250 ml round flask with Dimroth condensers and drying tubes.

Under stirring, 9.7 mmol oleoyl chloride (2.92 g) was added slowly. The reaction was stopped after 15 hours by lowering the temperature to 25° C. and adding 50 ml water.

The solution was extracted with 1% aqueous sulfuric acid (3×25 ml) and remaining solvent was removed by evaporation.

Released oleic acid was removed by chromatography on silica gel eluting with a gradient from 5% to 10% ethyl acetate in cyclohexane fortified with 0.1% acetic acid followed by evaporation of the solvent.

Ethyl 12-oleoyloxy-stearate was recovered in 84% (4.9 g) isolated yield.

PEG1500 mono-12-oleoyloxy-stearate 8.2 mmol (4.9 g) ethyl 12-oleoyloxy-stearate was mixed with 100 mmol (150 g) PEG1500 and 50 mg immobilized *C. antarctica* lipase B in a 500 ml round flask with stirring under vacuum (<1 mm Hg) at 75° C. for 39 hours.

The enzyme was removed by filtration and the product was extracted with ethyl acetate and saturated aqueous sodium chloride according to ISO-2268 [1972] at room temperature followed by solvent evaporation, dissolution in dry ethyl acetate, filtration and evaporation.

PEG1500 mono-12-oleoyloxy-stearate was recovered in 88% (14.8 g) isolated yield.

EXAMPLE 5

Synthesis of MePEG1200 12-palmitoyloxy-stearate

In general the reaction followed the way;
12-hydroxystearic acid→ethyl 12-hydroxystearate→ethyl 12-palmitoyloxy-stearate→MePEG1200 12-palmitoyloxy-stearate.

Ethyl 12-hydroxystearate
Was obtained according to Example 1.

Ethyl 12-palmitoyloxy-stearate
10 mmol (3.28 g) ethyl 12-hydroxystearate and 15 mmol (1.2 g) pyridine was dissolved in 100 ml MTBE at 50° C. in a 250 ml round flask with a Dimroth condenser and drying tube. Under stirring, 9.7 mmol (2.67 g) palmitoyl chloride was added slowly and allowed to react for 16 hours. The reaction was stopped by lowering the temperature to 25° C. and adding 50 ml water.

The solution was extracted with 1% aqueous sulfuric acid (3×25 ml) followed by saturated aqueous sodium bicarbonate (90 g/l, 3×25 ml) and water (3×25 ml). Remaining solvent was removed by evaporation.

Released palmitic acid was removed by chromatography on silica gel eluting with 5% ethyl acetate in cyclohexane fortified with 0.1% acetic acid followed by evaporation of the solvent. Ethyl 12-palmitoyloxy-stearate was recovered in 87% (4.6 g) isolated yield.

MePEG1200 12-palmitoyloxy-stearate
A portion of 3.76 g (6.97 mmol) ethyl 12-palmitoyloxy-stearate was mixed with 7.7 mmol MePEG1200 (9.2 g) and 50 mg Novozym 435 in a 100 ml round flask under vacuum (<1 mm Hg) with stirring at 75° C. for 200 hours.

The enzyme was removed by filtration and the product was extracted with ethyl acetate and saturated aqueous sodium chloride according to ISO-2268 [1972] at room temperature followed by solvent evaporation, dissolution in dry ethyl acetate, filtration and evaporation. MePEG1200 12-palmitoyloxy-stearate was recovered in 81% (9.75 g) isolated yield

EXAMPLE 6

Synthesis of MePEG2000 12-palmitoyloxy-stearate

In general the reaction followed the way;
12-hydroxystearic acid→ethyl 12-hydroxystearate→ethyl 12-palmitoyloxy-stearate→MePEG2000 12-palmitoyloxy-stearate.

Ethyl 12-hydroxystearate
Was obtained according to Example 1.

Ethyl 12-palmitoyloxy-stearate
10 mmol (3.28 g) ethyl 12-hydroxystearate and 15 mmol (1.2 g) pyridine was dissolved in 100 ml MTBE at 50° C. in a 250 ml round flask with a Dimroth condenser and drying tube. Under stirring, 9.7 mmol (2.67 g) palmitoyl chloride was added slowly and allowed to react for 16 hours. The reaction was stopped by lowering the temperature to 25° C. and adding 50 ml water.

The solution was extracted with 1% aqueous sulfuric acid (3×25 ml) followed by saturated aqueous sodium bicarbonate (90 g/l, 3×25 ml) and water (3×25 ml). Remaining solvent was removed by evaporation.

Released palmitic acid was removed by chromatography on silica gel eluting with 5% ethyl acetate in cyclohexane fortified with 0.1% acetic acid followed by evaporation of the solvent. Ethyl 12-palmitoyloxy-stearate was recovered in 87% (4.6 g) isolated yield.

MePEG2000 12-palmitoyloxy-stearate
A portion of 3.76 g (6.97 mmol) ethyl 12-palmitoyloxy-stearate was mixed with 7.7 mmol MePEG2000 (15.3 g) and 50 mg Novozym 435 in a 100 ml round flask under vacuum (<1 mm Hg) with stirring at 75° C. for 200 hours.

The enzyme was removed by filtration and the product was extracted with ethyl acetate and saturated aqueous sodium chloride according to ISO-2268 [1972] at room temperature followed by solvent evaporation, dissolution in dry ethyl acetate, filtration and evaporation.

MePEG2000 12-palmitoyloxy-stearate was recovered in 80% (14.0 g) isolated yield.

EXAMPLE 7

Synthesis of PEG 1500 mono-12-palmityloxy-stearate

The general reaction route is: palmityl alcohol→palmityl toluene-4-sulfonate→ethyl 12-palmityloxy-stearate→PEG1500 mono-12-palmityloxy-stearate Palmityl toluene-4-sulfonate
10 mmol palmityl alcohol and 20 mmol pyridine are dissolved in 100 ml dry dichloromethane. 10 mmol toluene4-sulphonyl chloride is slowly added and the mixture is heated to 40° C. with stirring for 1 hour. The reaction is cooled to room temperature and 25 ml cold water is added to stop the reaction. The mixture is washed with 3×50 ml cold, 1% aqueous sulfuric acid to remove the pyridine followed by 3×25 ml cold water and evaporation to yield palmityl toluene-4-sulfonate.

Ethyl 12-hydroxystearate
Is obtained in accordance with Example 1.

Ethyl 12-palmityloxy-stearate
Dissolve 10 mmol palmityl toluene-4-sulfonate, 10 mmol ethyl 12-hydroxystearate, 10 mmol anhydrous potassium carbonate and 0.5 mmol sodium iodide in 100 ml dry acetonitrile and heat to 81° C. with stirring for 6 hours. The reaction is cooled to room temperature. The solvent is evaporated and the products are suspended in MTBE and washed with 3×50 ml cold water. The solvent is evaporated to yield ethyl 12-palmityloxy-stearate.

PEG1500 mono-(12-palmityloxy-stearate)
10 mmol ethyl 12-palmityloxy-stearate is mixed with 100 mmol PEG1500 and 100 mg immobilized *Candida antarctica* lipase B in a 500 ml round flask with stirring under vacuum (<1 mm Hg) at 75° C. for 40 hours.

The enzyme is removed by filtration and the product is extracted with ethyl acetate and saturated-aqueous sodium chloride according to ISO-2268 [1972] followed by solvent evaporation, dissolution in dry ethyl acetate and filtration. The solvent is evaporated to yield PEG1500 mono-(12-palmityloxy-stearate).

EXAMPLE 8

Synthesis of BuPPG2500 12-stearoyloxy-stearate

The general reaction route is: 12-hydroxystearic acid→ethyl 12-hydroxystearate→ethyl 12-stearoyloxy-stearate→BuPPG2500 12-stearoyloxy-stearate Ethyl 12-stearoyloxy-stearate
Is obtained in accordance with Example 3.

BuPPG2500 12-stearoyloxy-stearate 10 mmol ethyl 12-stearoyloxy-stearate and 10.5 mmol BuPPG2500 (polypropylene glycol monobutyl ether of average molecular weight 2500 g/mol) are mixed with 500 mg Novozym 435 in a 500 ml round flask with stirring under vacuum (<1 mm Hg) at 75° C. for 100 hours.
The enzyme is removed by filtration to yield BuPPG2500 12-stearoyloxy-stearate.

EXAMPLE 9

Further Examples

Additional compounds according to the table 2 below were synthetisized using the same principal routes, involving the same enzyme, as described above in Examples 1-6.

TABLE 2

| Compounds | Isolated yield |
|---|---|
| PEG600 mono-12-hydroxystearate | 82% |
| PEG600 mono-12-acetoxy-stearate | 87% |
| PEG600 mono-12-hexanoyloxy-stearate | 73% |
| PEG600 mono-12-octanoyloxy-stearate | 95% |
| PEG600 mono-12-decanoyloxy-stearate | 93% |
| PEG1500 mono-12-lauroyloxy-stearate | 88% |
| PEG600 mono-12-myristoyloxy-stearate | 76% |
| PEG1500 mono-12-myristoyloxy-stearate | 86% |
| PEG1500 mono-12-palmitoyloxy-stearate | 82% |
| MePEG550 12-hydroxystearate | 90% |
| MePEG1200 12-stearoyloxy-stearate | 58% |
| MePEG2000 12-stearoyloxy-stearate | 77% |

Isolated yield is calculated based on the fatty acid reactant.

Some of the prepared compounds have been tested as described in Examples 10-12.

EXAMPLE 10

Haemolytic Activity

A static method for evaluating the haemolytic activity of compounds was used. In short, dog blood is processed to an erythrocyte suspension, which is then incubated (40 min at 37° C.) with varying concentrations of a surfactant. The incubation is terminated by centrifugation after which the plasma, now containing different amounts of haemoglobin, can be removed and analysed. The results obtained for various MePEG- and PEG mono-12-acyloxy-stearate esters compared with a reference substance (Tween 80), are summarized in tables 3-4.

TABLE 3

Haemolytic activity of monoesters of PEG600, MePEG550 and Tween 80.

| PEG600 mono-12-propionyloxy-stearate | | PEG600 mono-12-hexanoyloxy-stearate | | PEG600 mono-12-octanoyloxy-stearate | | MePEG550 12-hydroxystearate | | Tween 80 | |
|---|---|---|---|---|---|---|---|---|---|
| Conc mM | Hemolysis % | Conc mM | Hemolysis % | Conc mM | Hemolysis % | Conc mM | Hemolysis % | Conc mM | Hemolysis % |
| 0.6 | 104 | 0.6 | 83 | 0.6 | 88 | 1.0 | 25 | 1.0 | 0 |
|  |  | 0.7 | 92 | 0.7 | 102 | 5.0 | 86 | 5.0 | 2 |
|  |  |  |  |  |  | 10 | 79 | 10 | 29 |

TABLE 4

Haemolytic activity of monoesters of PEG1500, MePEG1200 and MePEG2000.

| PEG1500 mono-12-lauroyloxy-stearate | | PEG1500 mono-12-myristoyloxy-stearate | | PEG1500 mono-12-palmitoyloxy-stearate | | PEG1500 mono-12-stearoyloxy-stearate | | PEG1500 mono-12-oleoyloxy-stearate | |
|---|---|---|---|---|---|---|---|---|---|
| Conc mM | Hemolysis % | Conc mM | Hemolysis % | Conc mM | Hemolysis % | Conc mM | Hemolysis % | Conc mM | Hemolysis % |
| 1.0 | 0 | 3.1 | 0 | 1.0 | 0 | 1.0 | 0 | 0.8 | 0 |
| 1.5 | 0 | 6.2 | 0 | 3.0 | 0 | 3.1 | 0 | 1.9 | 0 |
| 3.0 | 11 | 7.7 | 0 | 5.0 | 0 | 5.1 | 0 | 3.7 | 0 |
| 5.0 | 98 | 10.8 | 0 | 7.0 | 0 | 7.2 | 0 | 6.0 | 0 |
|  |  | 12.3 | 0 | 9.9 | 0 | 10.2 | 0 | 8.2 | 0 |
|  |  | 15.4 | 0 |  |  |  |  | 11.2 | 0 |

| MePEG1200 12-palmitoyloxy-stearate | | MePEG2000 12-palmitoyloxy-stearate | | MePEG1200 12-stearoyloxy-stearate | | MePEG2000 12-stearoyloxy-stearate | |
|---|---|---|---|---|---|---|---|
| Conc mM | Hemolysis % | Conc mM | Hemolysis % | Conc mM | Hemolysis % | Conc mM | Hemolysis % |
| 1 | 0 | 1 | 0 | 1 | 0 | 1 | 0 |
| 5 | 0 | 5 | 0 | 5 | 0 | 5 | 0 |
| 10 | 0 | 10 | 0 | 10 | 0 | 10 | 0.2 |

As shown in Table 3 and Table 4, monoesters with short PEG or MePEG chains (average molecular weight below 1100) caused hemolysis at low concentrations. For example, PEG600 mono-12-propionyloxystearate, PEG600 mono-12-hexanoyloxystearate and PEG600 mono-12-octanoyloxystearate, caused total haemolysis at concentrations below 1 mM. MePEG550 mono-12-hydroxystearate (a compound representing the compounds disclosed in U.S. Pat. No. 6,365, 637 B1, Zirnstein et al) caused profound hemolysis at 1 mM and total hemolysis at 5 mM. Furthermore, the commercial product Tween 80 caused haemolysis at concentrations around 5 mM and above. In contrast to the PEG600 monoesters, the monoesters with longer PEG and MePEG chains did not cause any haemolysis at all up to 10 mM, except for PEG1500 mono-12-lauroyloxy-stearate which caused total hemolysis already at 5 mM.

EXAMPLE 11

Epithelial Cell Interaction

Possible interaction with epithelial cells in the form of CACO-2 cells monitored as transepitheliar electrical resistance (TEER) was studied for some of the compounds. In short, after an equilibration time of 60 min the buffer solution at the donor side was exchanged with a buffer solution containing a certain concentration of the surfactant and TEER was then measured after 8 hours.

In Table 5 the results for the PEG1500 mono-12-acyloxy-stearate, MePEG1200 12-acyloxy-stearates, MePEG2000 12-acyloxy-stearate and some reference substances tested at different concentrations, are shown. It is evident from Table 5 that even after 8 hours, no change in TEER is observed for monoesters with PEG chains or MePEG chains, having lengths corresponding to an average molecular weight of approximately 1200 or more, except for PEG1500 mono-12-lauroyloxy-stearate where there was a substantial decrease in TEER indicating some interaction with the epithelial cells. This is in contrast to the short PEG chains of Solutol HS 15, which are not well tolerated.

TABLE 5

TEER (measured in %) after 8 hours exposure

| Compound | Surfactant conc (mM) | | | |
|---|---|---|---|---|
| | 0.1 | 1 | 10 | 50 |
| Cremophor EL | 103 | 93 | 50 | 49 |
| Tween 80 | 96 | 99 | 89 | 65 |
| Solutol HS15 | 94 | 84 | 37 | 33 |
| PEG600 mono-12-hexanoyloxy-stearate | 89 | 43 | 39 | 37 |
| PEG1500 mono-12-lauroyloxy-stearate | 100 | 96 | 93 | 37 |
| PEG1500 mono-12-myristoyloxy-stearate | 104 | 100 | 104 | 98 |
| PEG1500 mono-12-palmitoyloxy-stearate | 98 | 105 | 103 | 101 |
| PEG1500 mono-12-stearoyloxy-stearate | 98 | 104 | 103 | 108 |
| PEG1500 mono-12-oleoyloxy-stearate | 105 | 104 | 95 | 108 |
| MePEG1200 12-palmitoyloxy-stearate | — | — | 94 | 103 |
| MePEG1200 12-stearoyloxy-stearate | — | — | 101 | 71 |
| MePEG2000 12-palmitoyloxy-stearate | — | — | 96 | 99 |
| MePEG2000 12-stearoyloxy-stearate | — | — | 98 | 96 |

— means no measurement performed.

EXAMPLE 12

Solubilizing Capacity

The solubilization capacity of the compounds of the invention and compounds of prior art for two poorly soluble (i.e. less than sparingly soluble) drug molecules, felodipine and griseofulvin, were tested. The solubility of griseofulvin in water is approximately 8.1 μg/ml, i.e. 23 μM [Mosharraf and Nyström, Int. J. Pharm., 1995, 122, 35-47] and the solubility of felodipine in water is 0.0008 mg/ml (2.1 μM, as the Mw=384 g/mol) [Corswant et al, J. Pharm. Sci., 1998, 87(2), 200-8]. The solubilization capacity for each surfactant was determined from the slope of the curve in a graph where the felodipine/griseofulvin concentration was plotted against the surfactant concentration at surfactant concentrations above CMC (critical micellar concentration).

$$\text{Solubilization capacity for } \textit{griseofulvin } \alpha_G = \frac{d[G]}{d[S]}$$

$$\text{and for } \textit{felodipine } \alpha_F = \frac{d[F]}{d[S]}$$

where
[G]=griseofulvin concentration [M]
[F]=felodipine concentration [M]
[S]=surfactant concentration [M] (above CMC)

The results are summarized in Table 6. The conclusion from these experiments is that the acylated HFA-PEG esters of this invention have better solubilization capacity than the prior art reference, the commercial product Solutol HS 15.

TABLE 6

Solubilization capacity for griseofulvin (αG) and felodipine (αF) for the acylated HFA-PEG-esters at 25° C. Solutol HS15 is a commercial product and is used as a reference.

| Compound | αG M/M | αF M/M |
|---|---|---|
| Solutol HS 15 | 0.015 | 0.15 |
| PEG1500 mono-12-lauroyloxy-stearate | 0.034 | 0.13 |
| PEG1500 mono-12-myristoyloxy-stearate | 0.044 | 0.31 |
| PEG1500 mono-12-palmitoyloxy-stearate | 0.032 | 0.32 |
| PEG1500 mono-12-stearoyloxy-stearate | 0.058 | 0.29 |

EXAMPLE 13

Felodipine Injectable Solution 12 g of PEG1500 mono-12-palmitoyloxy-stearate is dissolved in 988 g saline (0.9% w/w NaCl in water for injection). 380 mg felodipine is added and the mixture is stirred at room temperature until all felodipine is dissolved. The solution is filled under aseptic conditions into glass vials.

EXAMPLE 14

Extended Release Tablets Containing 5 mg Felodipine

The tablet are constructed according to the hydrophilic gel matrix principle.

First the solution I (according to below), comprising felodipine (active ingredient), propyl gallate and the surfactant PEG 1500-mono-12-palmitoyloxy-stearate, was made.

Secondly, the solution II was prepared.

The powders (III) were mixed in a mixer and moistened with Solution I until homogeneity.

The solution II was added and the mixing continued until homogeneity.

The obtained granulate was dried in a drying oven.

Thereafter it was milled and sieved to a suitable particle size distribution.

The granulate obtained was mixed with the powder IV, the lubricant, and mixing was continued for a total of 3 minutes. The mixture was compressed to tablets having an average weight of 227 mg, on a tabletting machine, using 9 mm circular concave punches.

|  | mg/tabl | grams/ 10000 tablets |
|---|---|---|
| Solution I |  |  |
| Felodipine | 5 | 50 |
| PEG1500 mono-palmitoyloxy-stearate | 5 | 50 |
| Propyl gallate | 0.06 | 0.6 |
| Ethanol | 30 | 300 |
| Solution II |  |  |
| Hydroxypropyl cellulose | 10 | 100 |
| Ethanol | 160 | 1600 |
| Powders III |  |  |
| Hydroxypropylmethylcellulose 50 cps | 100 | 1000 |
| Hydroxypropylmethylcellulose 10000 cps | 20 | 200 |
| Sodium Aluminium Silicate | 55 | 550 |
| Lactose | 28 | 280 |
| Powder IV |  |  |
| Sodium stearyl fumarate | 4.3 | 43 |

Tablets compressed at 17 kN having an average hardness of 71 N were tested for dissolution of felodipine, using a USP dissolution apparatus No. 2 (paddle), equipped with stationary baskets, operated at 100 rpm.

As dissolution medium 500 ml of 0.1 M phosphate buffer pH 6.5 with addition of 0.4% cetyl trimethyl ammonium bromide was used. The following results were obtained;

| | % Felodipin dissolved (n = 6) | | |
|---|---|---|---|
| | 1 hr | 4 hrs | 7 hrs |
| Min | 13 | 55 | 88 |
| Max | 14 | 61 | 96 |
| Average | 14 | 58 | 92 |

The tablets obtained may be used as cores in e.g a coating procedure with a pigmented HPMC solution.

EXAMPLE 15

Extended Release Tablets Containing 5 mg Felodipine

The tablets are constructed according to the hydrophilic gel matrix principle.

The tablets are prepared according to Example 14, except that the surfactant used in Example 14, PEG1500 mono-12-palmitoyloxy-stearate is exchanged to MePEG2000 12-stearoyloxy-stearate.

EXAMPLE 16

Extended Release Tablets Containing 5 mg Felodipine

The tablets are constructed according to the hydrophilic gel matrix principle.

The tablets are prepared according to Example 14, except that the surfactant used in Example 14, PEG1500 mono-12-palmitoyloxy-stearate is exchanged to MePEG 1200 12-palmitoyloxy-stearate.

EXAMPLE 17

Extended Release Tablets Containing 5 mg Felodipine

The tablets are constructed according to the hydrophilic gel matrix principle.

The tablets are prepared according to Example 14, except that the surfactant used in Example 14, PEG1500 mono-12-palmitoyloxy-stearate is exchanged to PEG1500 mono-12-oleoyloxy-stearate.

EXAMPLE 18

Extended Release Tablets Containing 5 mg Felodipine

The tablets are constructed according to the hydrophilic gel matrix principle.

The tablets are prepared according to Example 14, except that the surfactant used in Example 14, PEG1500 mono-12-palmitoyloxy-stearate is exchanged to BuPPG2500 12-stearoyloxy-stearate.

EXAMPLE 19

Solid Dispersion Formulation 5 g felodipine is dissolved in 150 g melted MePEG2000 12-stearoyloxy-stearate. The melt (continuously stirred) is filled into hard gelatine capsules. The capsules are cooled under controlled conditions.

EXAMPLE 20

Emulsion for Parenteral Use 0.5 g felodipine and 1.0 g soybean lecithin are dissolved in 98.5 g soybean oil. 5 g PEG1500 mono-12-palmitoyloxy-stearate is dissolved in 895 g of water for injection. A coarse emulsion is formed by mixing the oil phase with the aqueous phase using an ultraturrax mixer. The droplet size is further decreased by high-pressure homogenisation.

EXAMPLE 21

Self-emulsifying Drug Delivery Systems (SEDDS)

2 g felodipine is dissolved in 300 g of a Miglyol 812/PEG1500 mono-12-palmitoyloxy-stearate mixture (70/30 w/w). The mixture is then filled in soft gelatine capsules.

EXAMPLE 22

Suppository Formulation 5 g felodipine is dissolved in a molten mixture of 175 g PEG1500 mono-12-palmitoyloxy-stearate and 175 g PEG2000 and the mass is cast in appropriate moulds.

The invention claimed is:
1. A compound of the formula (I)

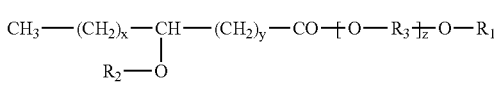

wherein:
$R_1$ is H or $C_1$-$C_4$ alkyl;
$R_2$ is a $C_{14}$ to $C_{22}$ acyl, alkyl or alkenyl group, wherein the acyl, alkyl or alkenyl group is linear or branched, and is optionally substituted with one or more substituents independently selected from the group consisting of: halogen, cyano, carboxy, carbamoyl, carbarnoyl($C_1$-$C_4$) alkyl, fluoromethyl, difluoromethyl, trifluoromethyl, mercapto, nitro, amino, ($C_1$-$C_4$)alkylamino, phenyl, naphthyl, phenyloxy, naphthyloxy, ($C_1$-$C_4$)alkylthio, and ($C_1$-$C_4$)alkylsulfinyl;
$R_3$ is ethylene, propylene, or branched propylene;
x is 2-18;
y is 1-17;
the sum of (x+y) is 3-19; and
z is 25-455.

2. The compound according to claim 1, wherein $R_1$ is H or $C_1$-$C_2$ alkyl.

3. The compound according to claim 1, wherein:
x is 2-15;
y is 4-17;
and the sum of (x+y) is 6-19.

4. The compound according to claim 1, wherein z is 25-228.

5. The compound according to claim 1, wherein:
$R_1$ is H or $C_1$-$C_2$alkyl;
$R_2$ is a $C_{14}$ to $C_{22}$ acyl, alkyl or alkenyl group, wherein the acyl, alkyl or alkenyl group is linear or branched, and is optionally substituted with one or more substituents independently selected from the group consisting of: halogen, cyano, carboxy, carbamoyl, carbamoyl($C_1$-$C_4$) alkyl, fluorormethyl, difluoromethyl, trifluoromethyl, mercapto, nitro, amino, ($C_1$-$C_4$)alkylamino, phenyl, naphthyl, phenyloxy, naphthyloxy, ($C_1$-$C_4$)alkylthio, and ($C_1$-$C_4$)alkylsulfinyl;
$R_3$ is ethylene, propylene or branched propylene;
x is 2-15;
y is 4-17;
the sum of (x+y) is 6-19; and
z is 25-228.

6. The compound according to claim 1, wherein $R_1$ is H.

7. The compound according to claim 1, wherein $R_1$ is $C_1$-$C_2$ alkyl.

8. The compound according to claim 1, wherein:
x is 2-12;
y is 7-17;
and the sum of (x+y) is 9-19.

9. The compound according to claim 1, wherein z is 25-57.

10. The compound according to claim 5, wherein:
$R_1$ is H or $C_1$-$C_2$ alkyl;
$R_2$ is a $C_{14}$ to $C_{22}$ acyl, alkyl or alkenyl group, wherein the acyl, alkyl or alkenyl group is linear or branched, and is optionally substituted with one or more substituents independently selected from the group consisting of: halogen, cyano, carboxy, carbamoyl, carbamoyl($C_1$-$C_4$) alkyl, fluoromethyl, difluoromethyl, trifluoromethyl, mercapto, nitro, amino, ($C_1$-$C_4$)alkylamino, phenyl, naphthyl, phenyloxy, naphthyloxy, ($C_1$-$C_4$)alkylthio, and ($C_1$-$C_4$)alkylsulfinyl;
$R_3$ is ethylene, propylene or branched propylene;
x is 2-12;
y is 7-17;
the sum of (x+y) is 9-19, and
z is 25-57.

11. The compound according to claim 1, wherein $R_1$ is methyl.

12. A formulation comprising a compound according to claim 1 and a compound requiring solubilization.

13. The formulation according to claim 12, wherein the compound requiring solubilization has a solubility of less than 33 mg/ml in water.

14. The formulation according to claim 12, wherein the compound requiring solubilization is a pharmaceutically active compound.

* * * * *